(12) United States Patent
Parker et al.

(10) Patent No.: US 8,923,984 B2
(45) Date of Patent: *Dec. 30, 2014

(54) KNITTED ELECTRODE ASSEMBLY FOR AN ACTIVE IMPLANTABLE MEDICAL DEVICE

(75) Inventors: John L. Parker, Roseville (AU); David Robinson, Bronte (AU)

(73) Assignee: Saluda Medical Pty Limited, Eveleigh, NSW (AU)

( * ) Notice: Subject to any disclaimer, the term of this patent is extended or adjusted under 35 U.S.C. 154(b) by 737 days.

This patent is subject to a terminal disclaimer.

(21) Appl. No.: 12/549,899

(22) Filed: Aug. 28, 2009

(65) Prior Publication Data

US 2010/0070008 A1 Mar. 18, 2010

(30) Foreign Application Priority Data

Sep. 17, 2008 (AU) ................................. 2008904838
Apr. 8, 2009 (AU) ................................. 2009901531
Apr. 8, 2009 (AU) ................................. 2009901534

(51) Int. Cl.
*A61N 1/05* (2006.01)
*A61M 25/00* (2006.01)
*A61N 1/375* (2006.01)

(52) U.S. Cl.
CPC ......... *A61N 1/0529* (2013.01); *A61M 25/0009* (2013.01); *A61N 1/375* (2013.01)
USPC ........................................................ 607/116

(58) Field of Classification Search
CPC ....... A61N 1/04; A61N 1/042; A61N 1/0424; A61N 1/0439; A61N 1/046
USPC ................ 607/37, 45, 2, 5; 600/378
See application file for complete search history.

(56) References Cited

U.S. PATENT DOCUMENTS

| | | | |
|---|---|---|---|
| 2,396,099 A * | 3/1946 | Hartwell | ........................ 338/208 |
| 3,773,034 A | 11/1973 | Burns et al. | |
| 4,411,276 A | 10/1983 | Dickhudt et al. | |
| 4,411,277 A | 10/1983 | Dickhudt | |
| 4,437,109 A | 3/1984 | Anthony et al. | |
| 4,543,090 A | 9/1985 | McCoy | |
| 4,549,556 A | 10/1985 | Tarjan et al. | |
| 5,314,451 A | 5/1994 | Mulier | |
| 5,466,252 A | 11/1995 | Soukup et al. | |
| 5,604,976 A | 2/1997 | Stobie et al. | |
| 5,679,026 A | 10/1997 | Fain et al. | |
| 5,720,099 A | 2/1998 | Parker et al. | |

(Continued)

FOREIGN PATENT DOCUMENTS

| | | |
|---|---|---|
| DE | 3510212 | 9/1986 |
| WO | 2004/058346 | 7/2004 |
| WO | 2004/084987 | 10/2004 |
| WO | 2008/048237 | 4/2008 |

OTHER PUBLICATIONS

International Search Report, PCT/US2009/055393; completion date Nov. 18, 2009; 4 pgs.

*Primary Examiner* — Carl H Layno
*Assistant Examiner* — Paula J Stice

(57) ABSTRACT

An active implantable medical device (AIMD). The AIMD comprises an electronics module; and a knitted electrode assembly comprising: at least one biocompatible, electrically non-conductive filament arranged in substantially parallel rows each stitched to an adjacent row, and at least one biocompatible, electrically conductive filament intertwined with the at least one non-conductive filament, and configured to be electrically connected to the electronics module.

34 Claims, 16 Drawing Sheets

(56) References Cited

U.S. PATENT DOCUMENTS

| | | |
|---|---|---|
| 6,198,969 B1 | 3/2001 | Kuzma |
| 6,321,126 B1 | 11/2001 | Kuzma |
| 6,421,569 B1 | 7/2002 | Treaba et al. |
| 6,662,035 B2 | 12/2003 | Sochor |
| 7,815,626 B1 * | 10/2010 | McFadden et al. ........... 604/525 |
| 2003/0186607 A1 | 10/2003 | Goldberg |
| 2003/0212319 A1 | 11/2003 | Magill |
| 2005/0165464 A1 | 7/2005 | Parker et al. |
| 2006/0129216 A1 * | 6/2006 | Hastings et al. .............. 607/115 |
| 2007/0202728 A1 | 8/2007 | Olson et al. |
| 2007/0251082 A1 | 11/2007 | Milojevic et al. |
| 2008/0147155 A1 * | 6/2008 | Swoyer et al. ................ 607/116 |
| 2008/0183257 A1 * | 7/2008 | Imran et al. ................... 607/117 |
| 2009/0018428 A1 * | 1/2009 | Dias et al. ..................... 600/388 |

* cited by examiner

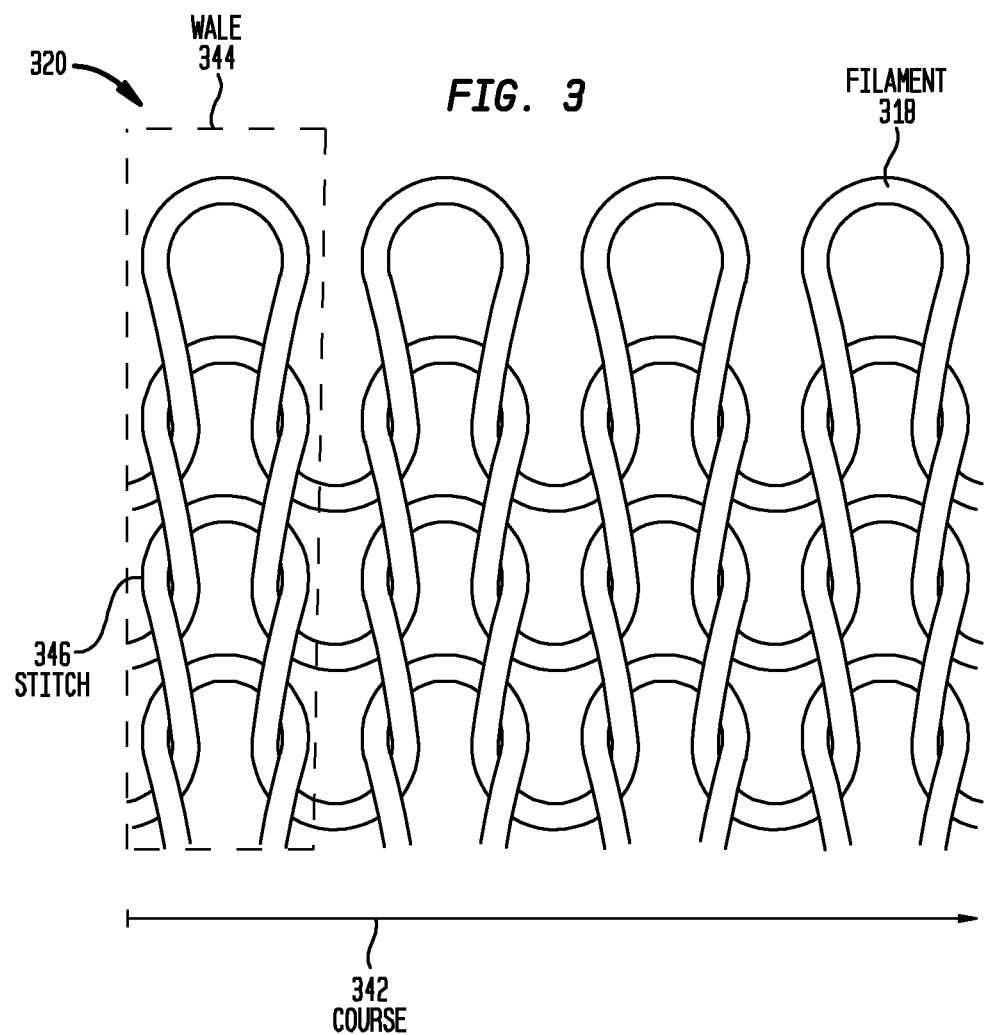

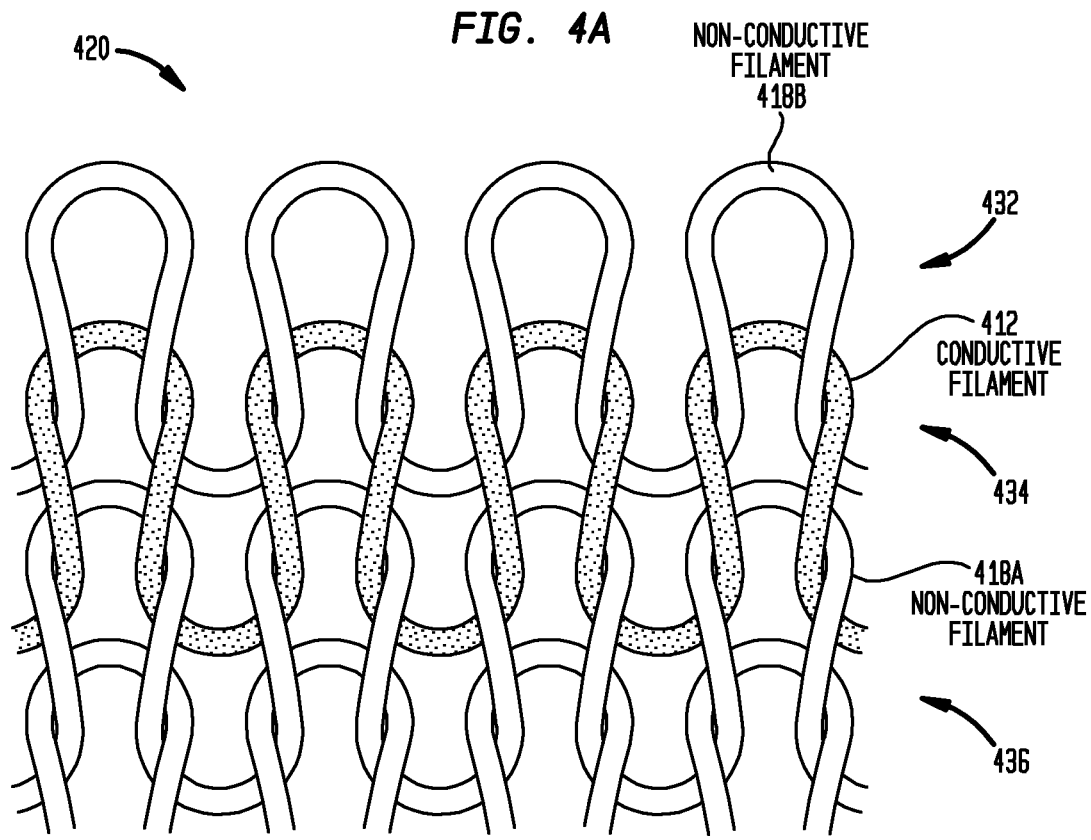
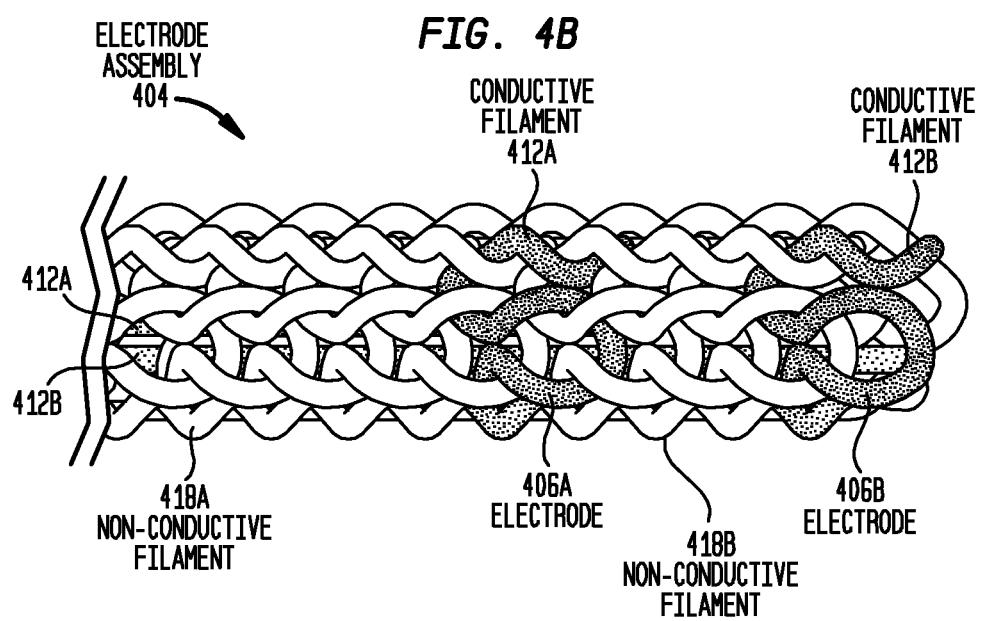

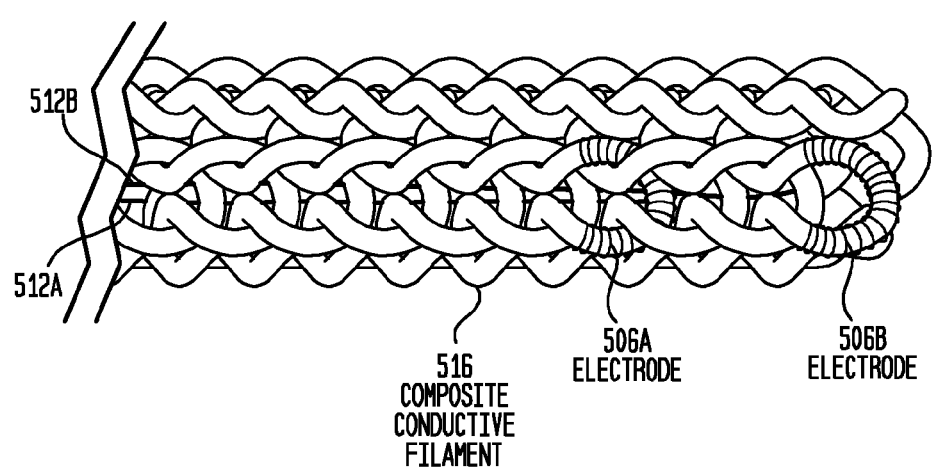

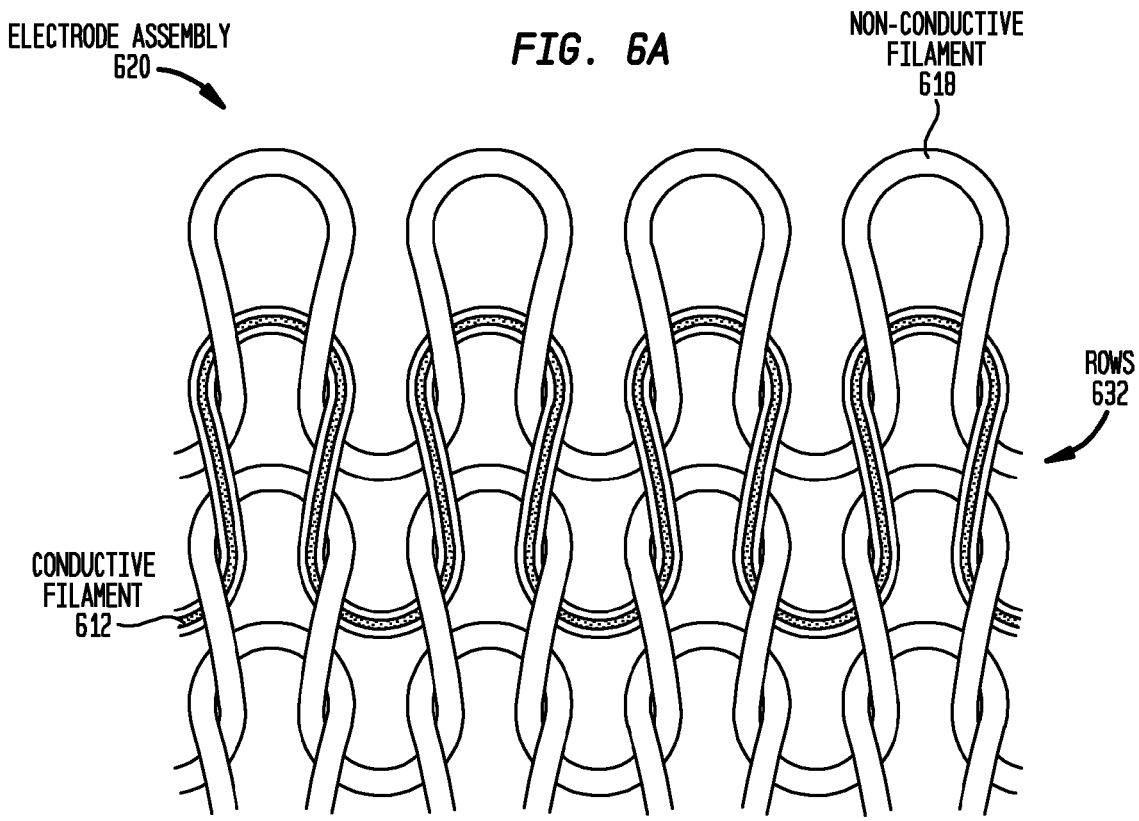
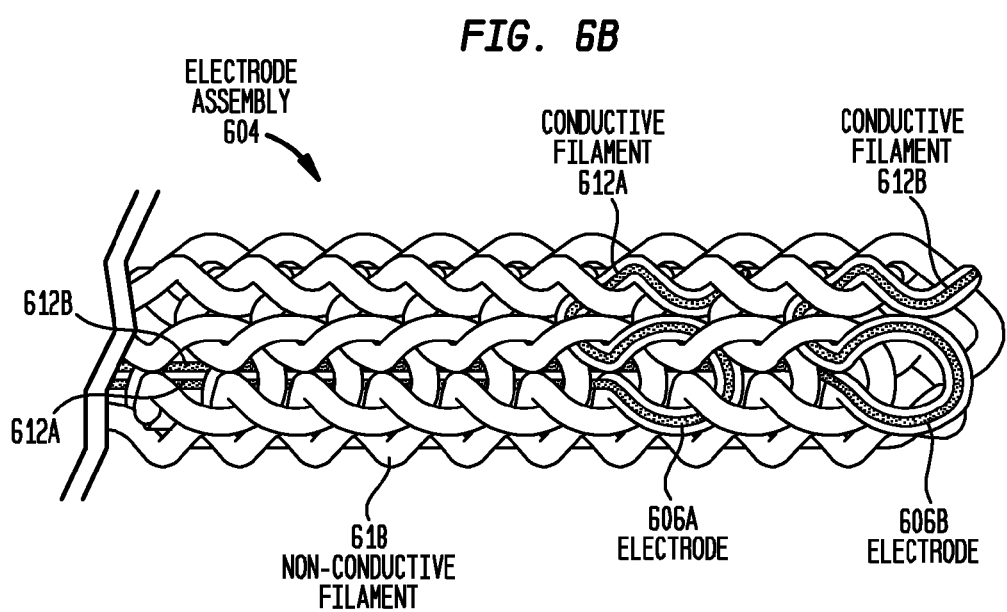

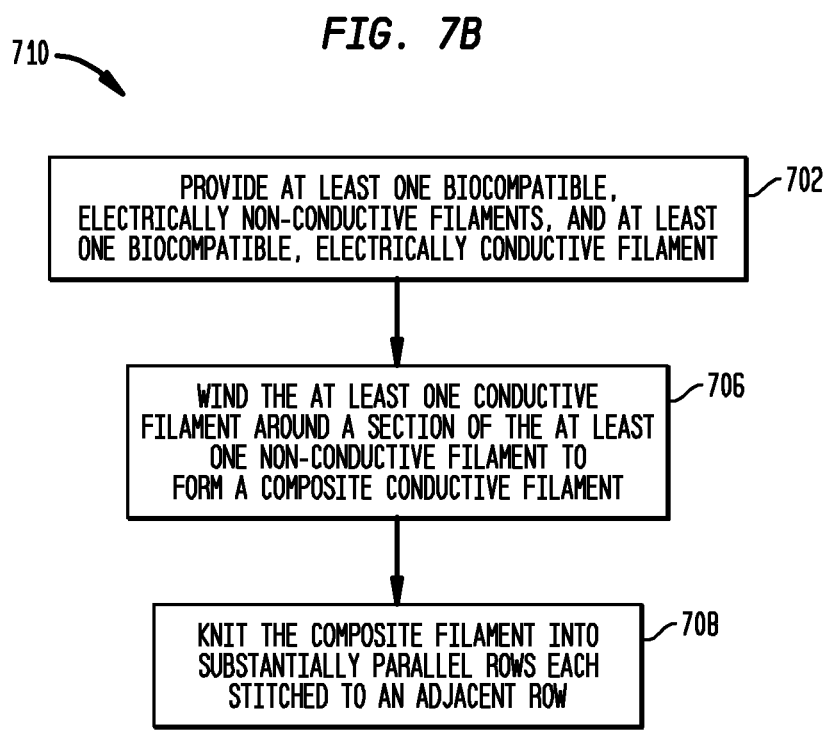

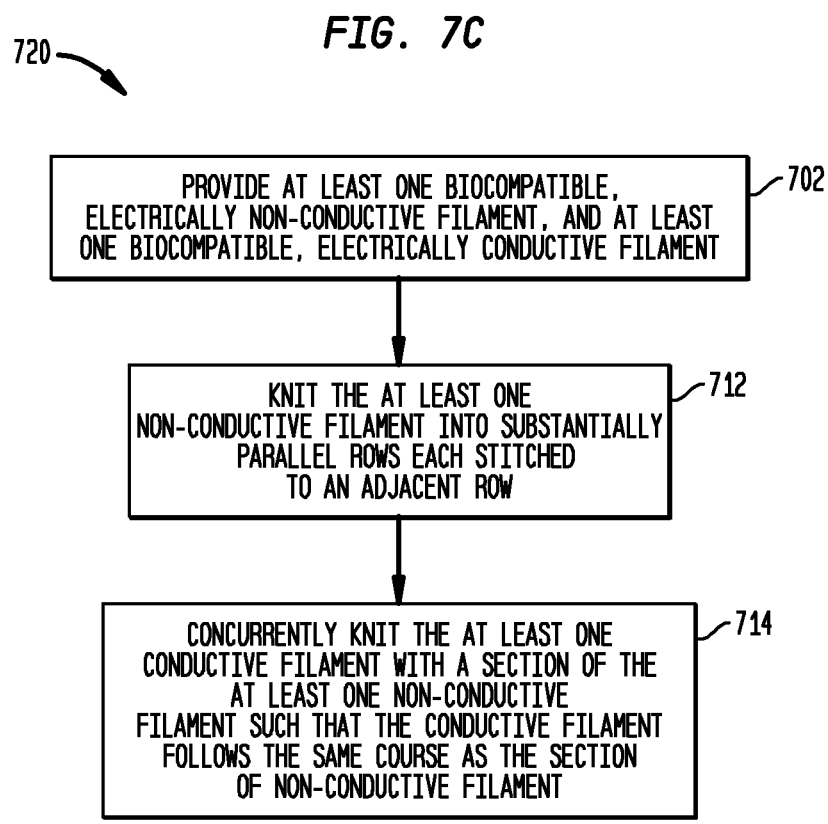

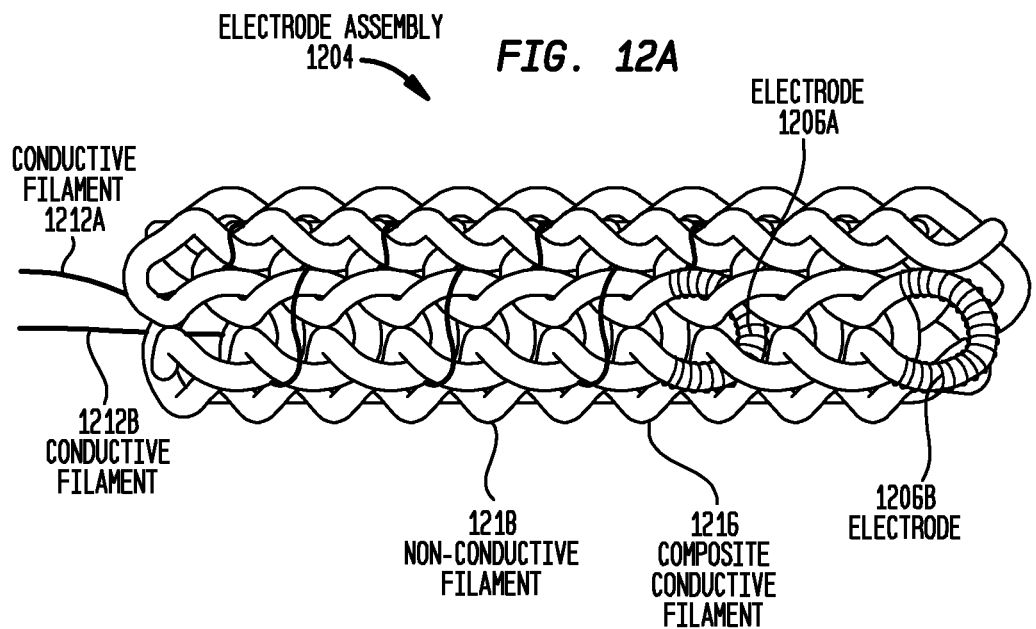
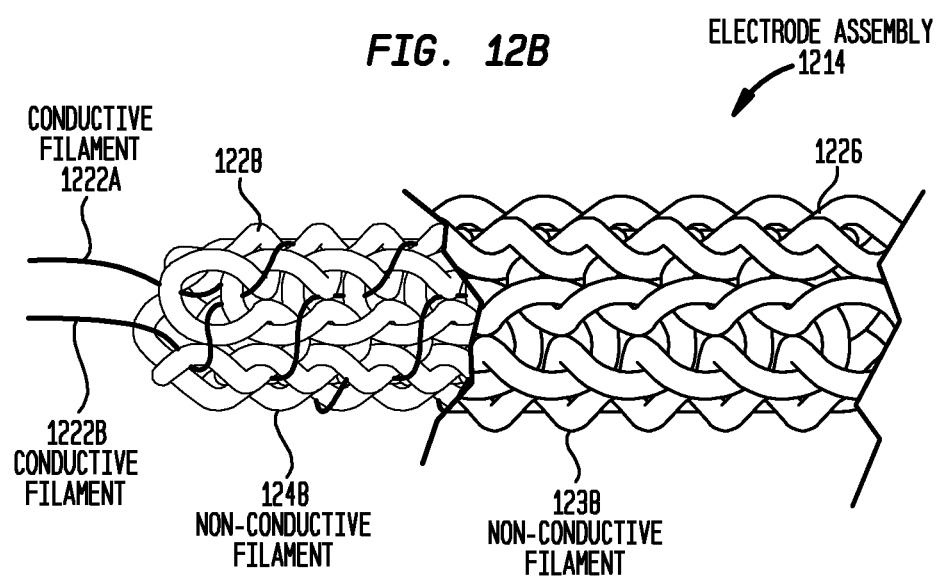

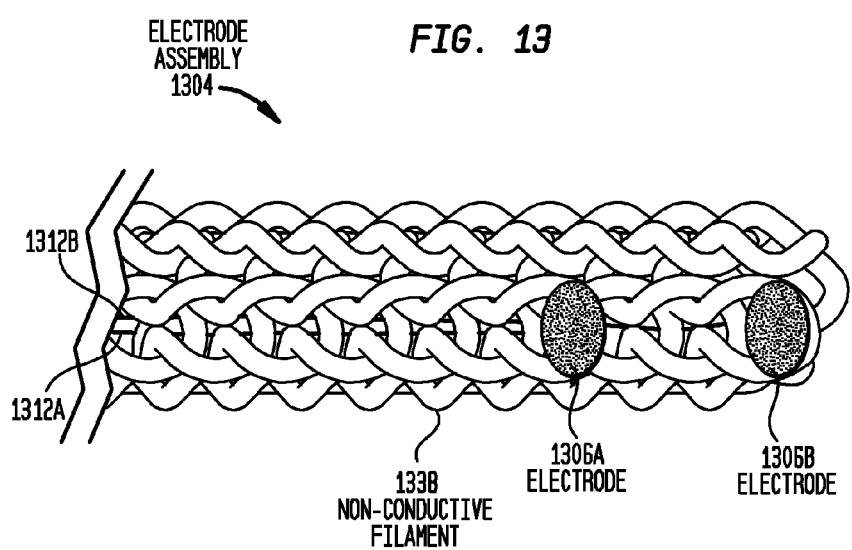

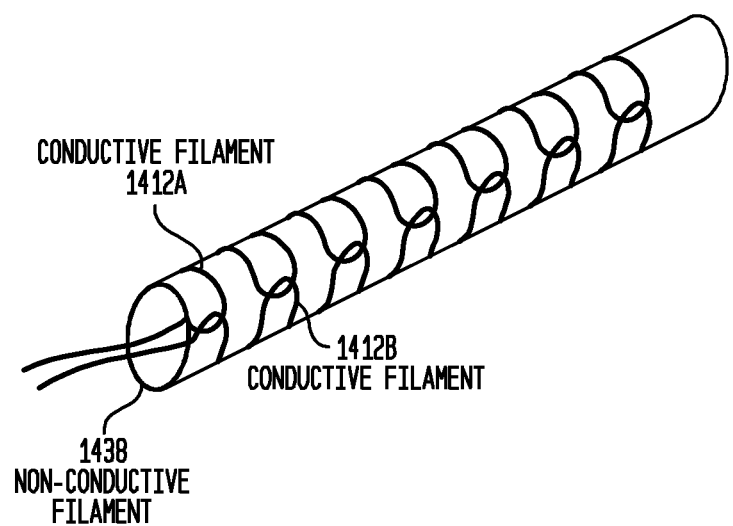

KNITTED ELECTRODE ASSEMBLY FOR AN ACTIVE IMPLANTABLE MEDICAL DEVICE

CROSS-REFERENCE TO RELATED APPLICATION

The present application claims priority from Australian Provisional Patent Application No. 2008904838, filed Sep. 17, 2008, Australian Provisional Patent Application No. 2009901534, filed Apr. 8, 2009, and Australian Provisional Patent Application No. 2009901531, filed Apr. 8, 2009, which are hereby incorporated by reference herein.

The present application is related to commonly owned and co-pending U.S. Utility patent application Ser. No. 12/549,457 entitled "Knitted Electrode Assembly And Integrated Connector For An Active Implantable Medical Device," filed Aug. 28, 2009, U.S. Utility patent application Ser. No. 12/549,801 "Knitted Catheter," filed Aug. 28, 2009, now abandoned, U.S. Utility patent application Ser. No. 12/549,875 "Bonded Hermetic Feed Through For An Active Implantable Medical Device," filed Aug. 28, 2009, now abandoned, U.S. Utility patent application Ser. No. 12/549,831 entitled "Stitched Components of An Active Implantable Medical Device," filed Aug. 28, 2009, and U.S. Utility patent application Ser. No. 12/549,786 entitled "Electronics Package For An Active Implantable Medical Device," filed Aug. 28, 2009, now abandoned, which are hereby incorporated by reference herein.

BACKGROUND

1. Field of the Invention

The present invention relates generally to active implantable medical devices (AIMDs), and more particularly, to a knitted electrode assembly for an AIMD.

2. Related Art

Medical devices having one or more active implantable components, generally referred to herein as active implantable medical devices (AIMDs), have provided a wide range of therapeutic benefits to patients over recent decades. AIMDs often include an implantable, hermetically sealed electronics module, and a device that interfaces with a patient's tissue, sometimes referred to as a tissue interface. The tissue interface may include, for example, one or more instruments, apparatus, sensors or other functional components that are permanently or temporarily implanted in a patient. The tissue interface is used to, for example, diagnose, monitor, and/or treat a disease or injury, or to modify a patient's anatomy or physiological process.

In particular applications, an AIMD tissue interface includes one or more conductive electrical contacts, referred to as electrodes, which deliver electrical stimulation signals to, or receive signals from, a patient's tissue. The electrodes are typically disposed in a biocompatible electrically non-conductive member, and are electrically connected to the electronics module. The electrodes and the non-conductive member are collectively referred to herein as an electrode assembly.

SUMMARY

In accordance with one aspect of the present invention, an active implantable medical device (AIMD) is provided. The AIMD comprises: an electronics module; and a knitted electrode assembly comprising: at least one biocompatible, electrically non-conductive filament arranged in substantially parallel rows each stitched to an adjacent row, and at least one biocompatible, electrically conductive filament intertwined with the at least one non-conductive filament, and configured to be electrically connected to the electronics module.

In accordance with another aspect of the present invention, a method for manufacturing a knitted implantable electrode assembly is provided. The method comprises: providing at least one biocompatible, electrically non-conductive filament, and at least one biocompatible, electrically conductive filament; and knitting the at least one non-conductive filament into substantially parallel rows each stitched to an adjacent row with the at least one conductive filament intertwined with the non-conductive filament.

BRIEF DESCRIPTION OF THE DRAWINGS

Aspects and embodiments of the present invention are described herein with reference to the accompanying drawings, in which:

FIG. 3 is a perspective view of a section of a knitted member;

FIG. 4A is a perspective view of a section of a knitted electrode assembly in accordance with embodiments of the present invention;

FIG. 4B is a side view of a section of a knitted electrode assembly in accordance with embodiments of the present invention;

FIG. 5C is a side view of a section of a knitted electrode assembly comprising a composite conductive filament of FIG. 5A, in accordance with embodiments of the present invention;

FIG. 6A is a perspective view of a section of a knitted electrode assembly comprising a conductive filament, in accordance with embodiments of the present invention;

FIG. 6B is a side view of a section of a knitted electrode assembly comprising a conductive filament of FIG. 6A, in accordance with embodiments of the present invention;

FIG. 7B is a detailed flowchart illustrating a method for manufacturing a knitted electrode assembly in accordance with embodiments of the present invention;

FIG. 7C is a detailed flowchart illustrating a method for manufacturing a knitted electrode assembly in accordance with embodiments of the present invention;

FIG. 12A is a side view of a section of a knitted electrode assembly in accordance with embodiments of the present invention;

FIG. 12B is a side view of a section of a knitted electrode assembly in accordance with embodiments of the present invention;

FIG. 13 is a side view of a section of a knitted electrode assembly in accordance with embodiments of the present invention; and FIG. 14 is a perspective view of a composite conductive filament in accordance with embodiments of the present invention;

DETAILED DESCRIPTION

Aspects of the present invention are generally directed to an active implantable medical device (AIMD) comprising an implantable, hermetically sealed electronics module and an electrode assembly formed using textile or fabric manufacturing methods.

A knitted electrode assembly in accordance with embodiments of the present invention comprises at least one biocompatible, electrically non-conductive filament arranged in substantially parallel rows each stitched to an adjacent row. The knitted electrode assembly further comprises at least one biocompatible, electrically conductive filament intertwined with the at least one non-conductive filament, and configured to be electrically connected to the electronics module.

Embodiments of the present invention are described herein primarily in connection with one type of AIMD, a neurostimulator, and more specifically a deep brain stimulator or spinal cord stimulator. Deep brain stimulators are a particular type of AIMD that deliver electrical stimulation to a patient's brain, while spinal cord stimulators deliver electrical stimulation to a patient's spinal column. As used herein, deep brain stimulators and spinal cord stimulators refer to devices that deliver electrical stimulation alone or in combination with other types of stimulation. It should be appreciated that embodiments of the present invention may be implemented in any brain stimulator (deep brain stimulators, cortical stimulators, etc.), spinal cord stimulator or other neurostimulator now known or later developed, such as cardiac pacemakers/defibrillators, functional electrical stimulators (FES), pain stimulators, etc. Embodiments of the present invention may also be implemented in AIMDs that are implanted for a relatively short period of time to address acute conditions, as well in AIMDs that are implanted for a relatively long period of time to address chronic conditions.

A knitted electrode assembly in accordance with embodiments of the present is not limited to devices that deliver electrical stimulation signals to a patient. For instance, in certain embodiments, the electrode assembly may be used to receive, record or monitor the physiological response of a patient's tissue to, for example, a therapy. In such embodiments, the electrodes receive a signal from the patient's tissue representing the physiological response. As described below, an electrode assembly of the present invention that delivers electrical stimulation signals to, or receives signals from, a patient's tissue may also include one or more other components, such as therapeutic agent delivery systems, sensors, etc., that interface with the patient's tissue.

Figure 1:
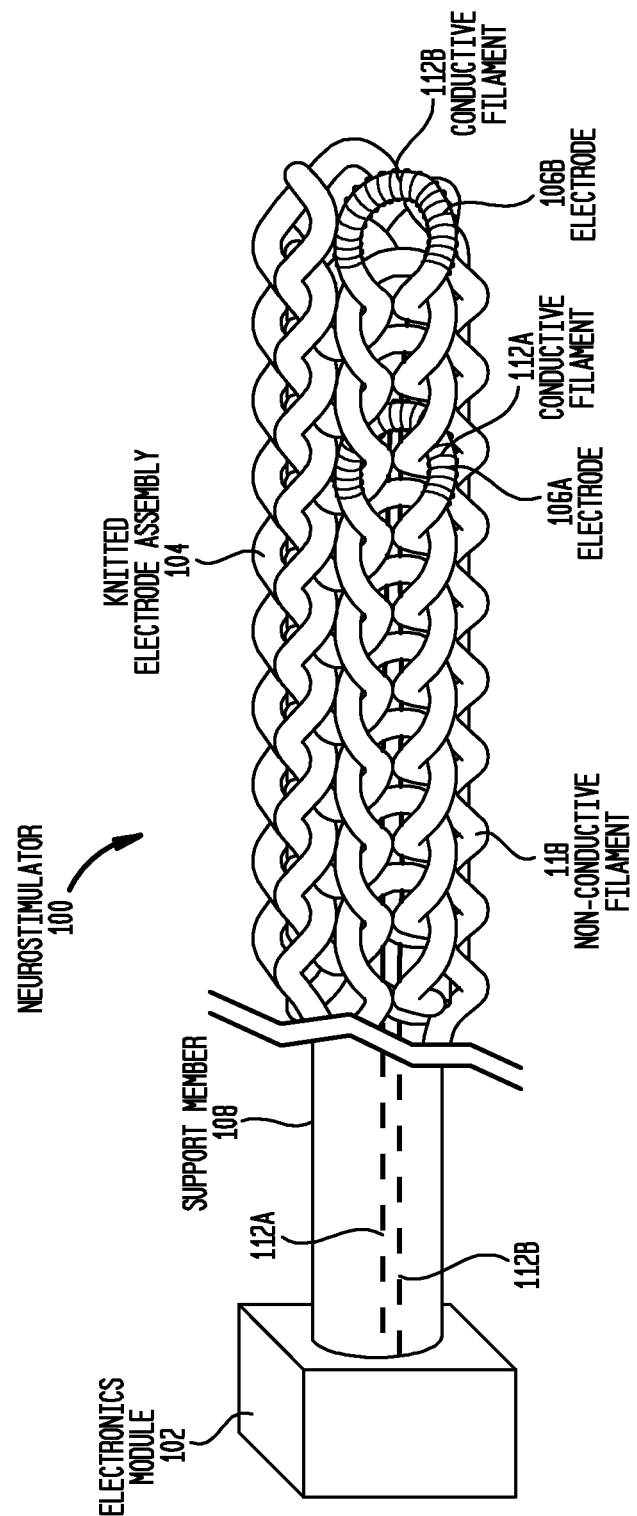
FIG. 1 is a perspective view of an exemplary active implantable medical device (AIMD), namely a neurostimulator, comprising a knitted electrode assembly in accordance with embodiments of the present invention.

FIG. 1 is a perspective view of an active implantable medical device (AIMD), namely a neurostimulator 100, in accordance with embodiments of the present invention. Neurostimulator 100 comprises an implantable, hermetically sealed electronics module 102, and a tissue interface, shown as knitted electrode assembly 104. As described in greater detail below, knitted electrode assembly 104 comprises a biocompatible, electrically non-conductive filament arranged in substantially parallel rows each stitched to an adjacent row. In the illustrative embodiments of FIG. 1, the parallel rows form an elongate tubular structure. However, as described below, the plurality of parallel rows may be arranged to form electrode assemblies having different shapes and dimensions.

Electrode assembly 104 further comprises two biocompatible, electrically conductive filaments 112 intertwined with non-conductive filament 118. In the specific embodiments of FIG. 1, conductive filaments 112 are conductive threads, fibers, wires or other types of filament that are wound around sections of non-conductive filament 118 prior to the knitting process. Also as detailed below, the term composite conductive filament is used herein to refer to a non-conductive filament having a conductive filament wound around a section thereof. As detailed below, conductive filaments 112 may be intertwined with non-conductive filament 118 in one of several other manners. As detailed below, the term wound is used herein to refer to wrap or encircle once or repeatedly around a filament.

In the embodiments of FIG. 1, the wound sections of conductive filaments 112 form electrodes 106 which deliver electrical stimulation signals to, or receive signals from, a patient's tissue. A second portion of each filament 112 extends through the interior of electrode assembly 104 to electrically connect electrodes 106 to electronics module 102.

As noted, the term filament is used to refer to both the conductive and non-conductive threads, fibers or wires that are used to form knitted electrode assembly 104. It should be appreciated that, as shown in FIG. 1, filaments of varying diameters and properties may be used to form electrode assembly 104. As such, the use of filament to refer to both conductive and non-conductive elements should not be construed to imply that the conductive and non-conductive elements have the same diameter or properties.

As shown, conductive filaments 112 extend through a resiliently flexible support member 108 that mechanically couples knitted electrode assembly 104 to electronics module 102. Although FIG. 1 illustrates embodiments in which support member 108 connects knitted electrode assembly 104 to electronics module 102, it should be appreciated that in other embodiments knitted electrode assembly 104 may be directly connected to the electronics module. Such embodiments are described in commonly owned and co-pending U.S. Utility Patent Application entitled "Knitted Electrode Assembly and Integrated Connector for an Active Implantable Medical Device," filed Aug. 28, 2009, the content of which is hereby incorporated by reference herein.

Figure 2:
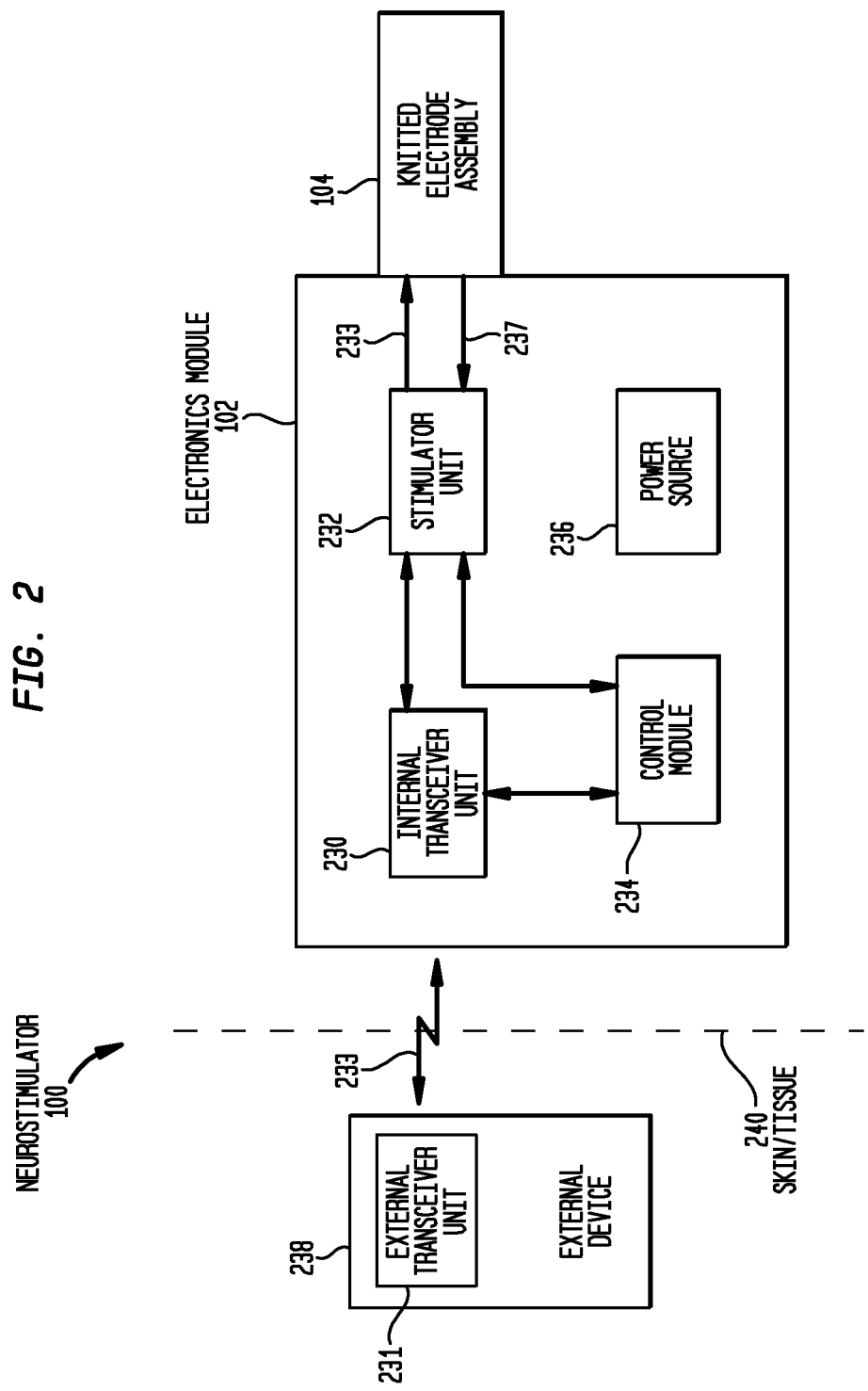
FIG. 2 is a functional block diagram of the neurostimulator illustrated in FIG. 1, in accordance with embodiments of the present invention.

FIG. 2 is a functional block diagram illustrating one exemplary arrangement of electronics module 102 of neurostimulator 100 of the present invention. In the embodiments of FIG. 2, electronics module 102 is implanted under a patient's skin/tissue 240, and cooperates with an external device 238. External device 238 comprises an external transceiver unit 231 that forms a bi-directional transcutaneous communication link 233 with an internal transceiver unit 230 of electronics module 102. Transcutaneous communication link 233 may be used by external device 238 to transmit power and/or data to electronics module 102. Similarly, transcutaneous communication link 233 may be used by electronics module 102 to transmit data to external device 238.

As used herein, transceiver units 230 and 231 each include a collection of one or more components configured to receive and/or transfer power and/or data. Transceiver units 230 and 231 may each comprise, for example, a coil for a magnetic inductive arrangement, a capacitive plate, or any other suitable arrangement. As such, in embodiments of the present invention, various types of transcutaneous communication, such as infrared (IR), electromagnetic, capacitive and inductive transfer, may be used to transfer the power and/or data between external device 238 and electronics module 102.

In the specific embodiment of FIG. 2, electronics module 102 further includes a stimulator unit 232 that generates electrical stimulation signals 233. Electrical stimulation signals 233 are delivered to a patient's tissue via electrodes 106 (FIG. 1) of knitted electrode assembly 104. Stimulator unit 232 may generate electrical stimulation signals 233 based on, for example, data received from external device 238, signals received from a control module 234, in a pre-determined or pre-programmed pattern, etc.

As noted above, in certain embodiments, electrodes 106 of knitted electrode assembly 104 are configured to record or monitor the physiological response of a patient's tissue. In such embodiments, signals 237 representing the recorded response may be provided to stimulator unit 232 for forwarding to control module 234, or to external device 238 via transcutaneous communication link 233.

In the embodiments of FIG. 2, neurostimulator 100 is a totally implantable medical device that is capable of operating, at least for a period of time, without the need for external device 238. Therefore, electronics module 102 further comprises a rechargeable power source 236 that stores power received from external device 238. The power source may comprise, for example, a rechargeable battery. During operation of neurostimulator 100, the power stored by the power source is distributed to the various other components of electronics module 102 as needed. For ease of illustration, electrical connections between power source 236 and the other components of electronics module 102 have been omitted. FIG. 2 illustrates power source 236 located in electronics module 102, but in other embodiments the power source may be disposed in a separate implanted location.

FIG. 2 illustrates specific embodiments of the present invention in which neurostimulator 100 cooperates with an external device 238. It should be appreciated that in alternative embodiments, deep brain stimulation 100 may be configured to operate entirely without the assistance of an external device.

As noted above, embodiments of the knitted electrode assembly comprise at least one biocompatible, electrically non-conductive filament arranged in substantially parallel rows stitched to an adjacent row, with at least one biocompatible, electrically conductive filament intertwined with the non-conductive filament. Knitting is a technique for producing a two or three-dimensional structure from a linear or one-dimensional yarn, thread or other filament (collectively and generally referred to as "filaments" herein) to produce an intermeshed loop structure. A stitch in knitting includes the use of one or more loops to connect filaments to form the structure. There are two primary varieties of knitting, known as weft knitting and warp knitting. FIG. 3 is a perspective view of a section of a knitted structure 320 formed by weft knitting a single filament 318.

As shown in FIG. 3, a filament course 342 is a generally meandering path of the filament that create substantially straight and parallel rows of filament loops. The filament course 342, is substantially perpendicular to the sequences of interlocking stitches 346. A sequence of stitches 346 is referred to as a wale 344. In weft knitting, the entire knitted structure may be manufactured from a single filament by adding stitches 346 to each wale 344 in turn. In contrast to the embodiments illustrated in FIG. 3, in warp knitting, the wales run roughly parallel to the filament course 342.

It should be appreciated that embodiments of the present invention may be implemented using weft or warp knitting. Furthermore, embodiments of the present invention may use circular knitting or flat knitting. Circular knitting creates a seamless tube, while flat knitting creates a substantially planar sheet.

Electrode assemblies in accordance with embodiments of the present invention may be knitted using automated knitting methods known in the art, or alternatively using a hand knitting process. It should be appreciated that the knitting method, filament diameter, number of needles and/or the knitting needle size may all affect the size of the stitches and the size of the resulting electrode assembly. As such, the size and shape of the assembly is highly customizable.

FIGS. 4A and 4B illustrate embodiments of the present invention in which an electrode assembly is formed by alternately knitting with conductive and non-conductive filaments. A portion 420 of such a flat knitted structure is shown in FIG. 4A.

As shown in FIG. 4A, a first non-conductive filament 418A is knitted into a plurality of substantially parallel rows 436. A first conductive filament 412 is stitched to one of the rows 436 such that conductive filament 412 forms an additional row 434 that is parallel to rows 436. A second non-conductive filament 418B is stitched to row 434 such that the second non-conductive filament forms one or more rows 432 that are parallel to rows 434 and 436. For ease of illustration, a single conductive row 434 and a single non-conductive row 432 are shown. It should be appreciated that additional conductive or non-conductive rows may be provided in alternative embodiments. It should also be appreciated that in alternative embodiments each conductive row does not necessarily form a full row. For instance, a conductive filament could be used to form a number of stitches within a row, and a non-conductive filament could be used to complete the row.

FIG. 4B illustrates an elongate electrode assembly 404 circular knitted in accordance with the structure of FIG. 4A. In the embodiments of FIG. 4B, a plurality of rows are knitted from a first non-conductive filament 418A and form a first section of electrode assembly 404. A first conductive filament 412A forms a row that is knitted to the rows of non-conductive filament 418A. The row of first conductive filament 412A forms an electrode 406A that may be used to deliver electrical stimulation signals to, and/or receive signals from, a patient's tissue.

In the embodiments of FIG. 4B, a second non-conductive filament 418B is knitted to the row of conductive filament 412A to form an additional non-conductive section of electrode assembly 404. A second conductive filament 412B forms a row that is knitted to the rows of non-conductive filament 418B. Similar to the row of conductive filament 412B, the row of second conductive filament 412B forms an electrode 406B that may be used to deliver electrical stimulation signals to, and/or receive signals from, a patient's tissue. As used herein, conductive filaments 412A and 412B are referred to as being intertwined with non-conductive filament 418B.

As noted above, conductive filaments 412A, 412B are configured to be electrically connected to an electronics module. As such a section of the each filament 412 extends proximally from electrodes 406 through the interior of electrode assembly 404 for connection to an electronics module.

A variety of different types and shapes of conductive filaments may be used to knit an electrode assembly in accordance with embodiments of the present invention. In one embodiment, the conductive filament is a fiber manufactured from carbon nanotubes. Alternatively, the conductive filament is a platinum or other biocompatible conductive wire. Such wires may be given suitable surface treatments to increase their surface area (e.g. forming a layer of iridium oxide on the surface of platinum, utilizing platinum "blacking," or coating the wire with carbon nanotubes). In other embodiments, the conductive filament comprises several grouped strands of a conductive material. In other embodiments, the filament may be a composite filament formed from two or more materials to provide a desired structure. In certain such embodiments, the properties of the composite filament may change along the length thereof. For example, certain portions of the composite filament may be conductive, while portions are non-conductive. It would also be appreciated that other types of conductive filaments may also be used. Furthermore, although embodiments of the present invention are described using tubular or round fibers, it would be appreciated that other shapes are within the scope of the present invention.

As noted above, conductive filaments in accordance embodiments of the present invention are intertwined with a non-conductive filament to form the electrode assembly. While a majority of the intertwined portion is an exposed conductive element, the remainder of the conductive filament may be insulated. In one such embodiment, a length of suitably insulated conductive filament (e.g. parylene coated platinum wire) is provided and the insulation is removed from the section that is to be intertwined, leaving the remainder of the filament with the insulated coating.

A variety of non-conductive filaments may be used to knit an electrode assembly in accordance with embodiments of the present invention. In one embodiment, the non-conductive filament is a biocompatible non-elastomeric polymer material. In another embodiment, the non-conductive filament is a biocompatible elastomeric material. For example, the elastomeric material may comprise, for example, silicone, silicone/polyurethane, silicone polymers, or other suitable materials including AORTech® and PBAX. Other elastomeric polymers that provide for material elongation while providing structural strength and abrasion resistance so as to facilitate knitting may also be used. It should be appreciated that other types of non-conductive filaments may also be used.

In embodiments in which an elastomeric non-conductive filament is used, the filament may be knitted under tension to reduce the final size of the electrode assembly, or portions thereof. The knitting of filaments under tension to form an electrode assembly is described in commonly owned and co-pending U.S. Utility Patent Application entitled Knitted Electrode Assembly and Integrated Connector for an Active Implantable Medical Device," filed Aug. 28, 2009, the content of which is hereby incorporated by reference herein.

In a further embodiment, a non-conductive filament comprises a drug-eluting polymer. In such embodiments, drugs appropriate to the application may be incorporated into the structure so as to be automatically dispensed once the electrode assembly is implanted. In alternative embodiments, fibers may be coated with any of a number of materials that provide a therapeutic benefit. For example, in one embodiment the fibers may receive an anti-fibrogenic coating that prevents attachment to tissue. In other embodiments the fibers may be coated with a therapeutic material which promotes healing. In still further embodiments, the non-conductive filament comprises a thermo-softening plastic material, such as polypropylene. As described below, the thermo-softening plastic material allows the knitted structure to be formed into a variety of shapes using, for example, molding, sintering, etc.

Figure 5A:
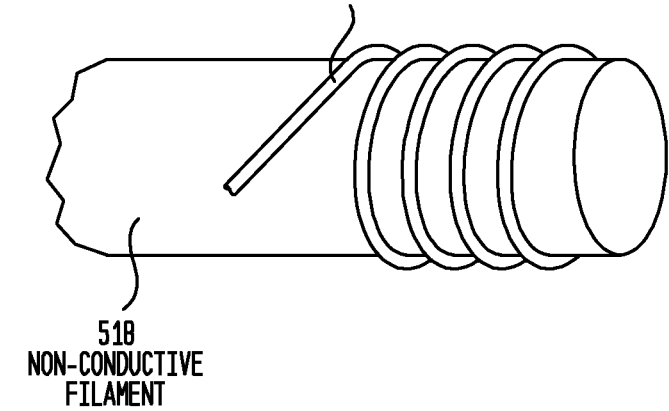
FIG. 5A is a perspective view of a composite conductive filament in accordance with embodiments of the present invention.
Figure 5B:
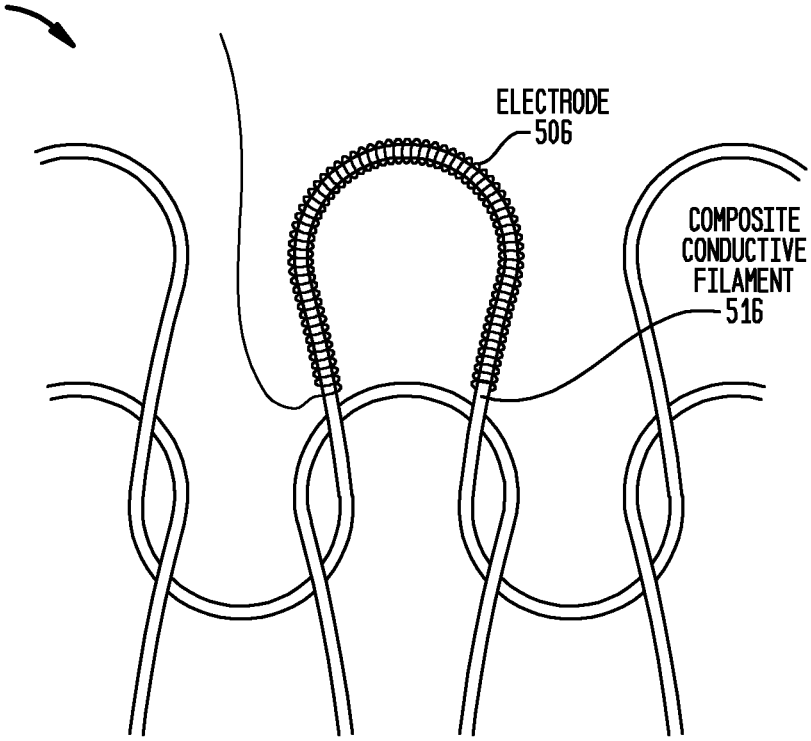
FIG. 5B is a perspective view of a section of a knitted electrode assembly comprising a composite conductive filament of FIG. 5A, in accordance with embodiments of the present invention.

As noted above, in one embodiment of the present invention a composite conductive filament is used to form an electrode assembly. FIGS. 5A-5C illustrate such embodiments in greater detail. As shown in FIG. 5A, a composite conductive filament 516 is formed by winding a section of a conductive filament 512 around a section of a non-conductive filament 518. Conductive filament 512 may be loosely or tightly wound onto non-conductive filament 518, and is referred to herein as being intertwined with non-conductive filament 518.

As noted, the term filament is used to refer to both the conductive and non-conductive threads, fibers or wires that are used to form a knitted electrode assembly. It should be appreciated that, as shown in FIGS. 5A-5C, filaments of varying diameters and properties may be used. As such, the use of filament to refer to both conductive and non-conductive threads, fibers and wires should not be construed to imply that the conductive and non-conductive elements have the same diameter or properties.

In certain embodiments of FIG. 5A, non-conductive filament 518 comprises a thermo-softening plastic material. The use of a thermo-softening filament allows conductive filament 512 to be wound around non-conductive filament 518 while the non-conductive filament is in a softened state. This ensures that conductive filament 512 is well integrated into non-conductive filament 518 so as to reduce any difference in the size of the stitches in the electrode area when compare to those in the non-conductive areas of a formed electrode assembly. As noted, conductive filament 512 may be loosely or tightly wound onto non-conductive filament 518. A loose winding provides integration of the two filaments and provides a compliant structure to manage fatigue. A tight winding provides substantially the same benefits, but also increases the amount of conductive filament in a single stitch. An alternative composite conductive filament is formed using a cording method as described below with reference to FIG. 14.

FIG. 5B is a perspective view of a section of a flat knitted electrode assembly 520 formed from composite conductive filament 516. In these embodiments, electrode assembly 520 comprises a substantially planar member. FIG. 5C is a side view of the distal portion of a circular knitted electrode assembly 504 formed using composite conductive filament 516. In these embodiments, electrode assembly 504 comprises an elongate tubular member.

When electrode assemblies 520, 504 of FIGS. 5B and 5C are formed, the conductive portions of composite conductive filament 516 (i.e. the portions of conductive filament 512 wound around non-conductive filament 518) form electrode 506 that may be used to deliver electrical stimulation signals to, and/or receive signals from, a patient's tissue.

FIGS. 6A and 6B illustrate other embodiments of a knitted electrode assembly having at least one conductive filament intertwined with a non-conductive filament in accordance with aspects of the present invention. More specifically, FIGS. 6A and 6B illustrate embodiments of the present invention in which an electrode assembly is formed by concurrently knitting a conductive filament with a non-conductive filament.

FIG. 6A illustrates a portion of a flat knitted electrode assembly 620. As shown, a non-conductive filament 618 is knitted into a plurality of parallel rows 632. A conductive filament 612 is concurrently knit with non-conductive filament 618 such that the conductive filament and the non-conductive filament 618 follow the same course. FIG. 6B illustrates an alternative structure in which the parallel rows of non-conductive filament 618 form an elongate tubular structure.

In the embodiments of FIGS. 6A and 6B, conductive filaments 612 are concurrently knitted with a section of non-conductive filament 618 such that conductive filaments 612 follow the same course as the section of non-conductive filament 618. In this arrangement, conductive filaments 612 are positioned on the exterior surface of electrode assemblies 604, 620. The concurrently knit sections of conductive filaments 612 are referred to as being intertwined with non-conductive filament 618. The intertwined portions of conductive filaments 612A, 612B each form an electrode 606A, 606B, respectively, that may be used to deliver electrical stimulation signals to, and/or receive signals from, a patient's tissue.

In the embodiments of FIG. 6B, conductive filaments 612A, 612B are configured to be electrically connected to an electronics module. As such a section of the each filament 612 extends proximally from the intertwined portions of the filament through the interior of electrode assembly 604 for connection to an electronics module.

Although FIGS. 6A and 6B illustrate embodiments in which the conductive filaments are positioned on the exterior surface of the knitted structure, it should be appreciated that in alternative embodiments the conductive filaments may in the interior of the electrode assembly. For example, if the electrode assembly is filled with a gel as described elsewhere herein, or is open to bodily fluids, an internal conductive surface may deliver electrical stimulation signals to the patient.

Figure 7A:
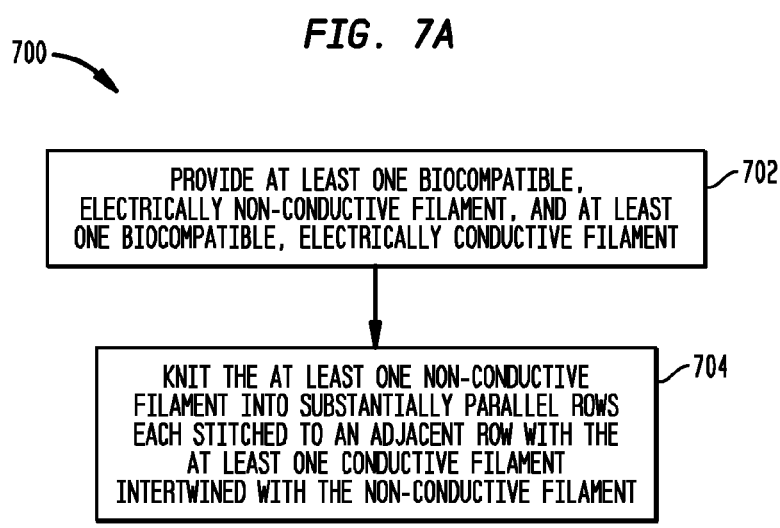
FIG. 7A is a high level flowchart illustrating a method for manufacturing a knitted electrode assembly in accordance with embodiments of the present invention.

FIG. 7A is a flowchart illustrating a method 700 for manufacturing a knitted implantable electrode assembly in accordance with embodiments of the present invention. As shown, method 700 begins at block 702 where at least one biocompatible, electrical non-conductive filament, and at least one biocompatible, electrically conductive filament are provided. As noted above, numerous different types of non-conductive and conductive filaments may be provided. After the filaments have been provided, the method proceeds to block 704 where the at least one non-conductive filament is knitted into substantially parallel rows each stitched to an adjacent row. The at least one conductive filament intertwined with the at least one non-conductive filament.

FIG. 7B is a flowchart illustrating a variation of method 700 of FIG. 7A, referred to as method 710. Method 710 begins at block 702 where, as discussed above with reference to FIG. 7A, at least one biocompatible, electrical non-conductive filament, and at least one biocompatible, electrically conductive filament are provided. After the filaments have been provided, the method proceeds to block 706 where a section of the at least one conductive wire is wound around the at least non-conductive filament to form a composite conductive filament. An exemplary composite conductive filament is described above with reference to FIGS. 5A-5C. At block 708, the composite conductive filament is knitted into substantially parallel rows, each row stitched to an adjacent row. Upon forming the knitted structure, the conductive portion of the composite conductive filament forms an electrode that may be used to deliver electrical stimulation signals to, and/or receive signals from, a patient's tissue.

FIG. 7C is a flowchart illustrating another variation of method 700 of FIG. 7A, referred to as method 720. Method 720 begins at block 702 where, as discussed above with reference to FIG. 7A, at least one biocompatible, electrical non-conductive filament, and at least one biocompatible, electrically conductive filament are provided. After the filaments have been provided, the method proceeds to block 712 where the at least one non-conductive filament is knitted into substantially parallel rows each stitched to an adjacent row. Concurrently with the knitting of the at least one non-conductive filament, at block 714 the at least one conductive filament is knitted with a section of the at least non-conductive filament. The conductive filament is concurrently knit with the at least one non-conductive filament such that the conductive filament follows the same course as the section of the at least one non-conductive filament, and such that the conductive filament is positioned on the exterior surface of the electrode assembly. Upon forming the knitted structure, the concurrently knit portion of the conductive filament forms an electrode that may be used to deliver electrical stimulation signals to, and/or receive signals from, a patient's tissue.

Figure 8:
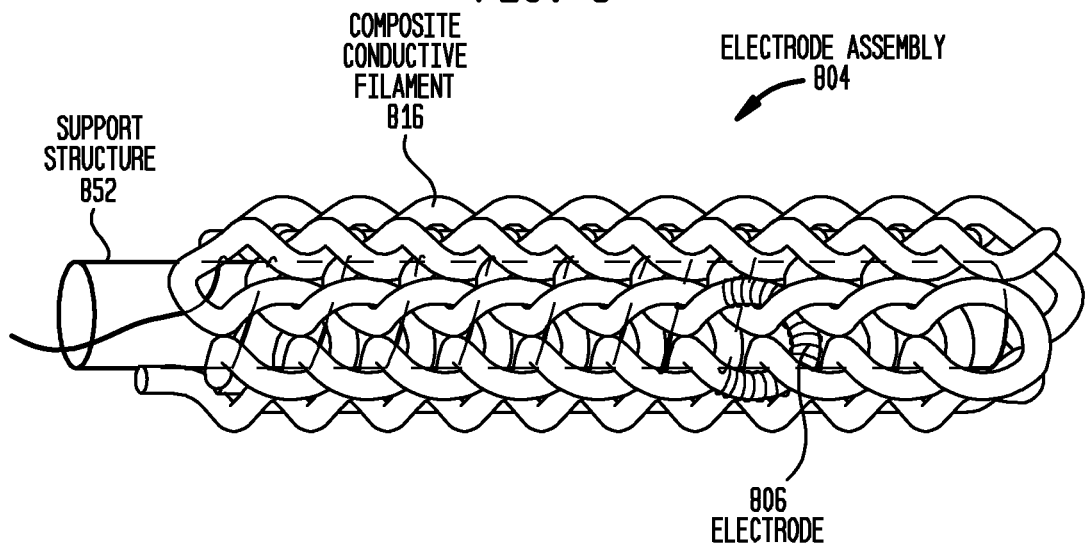
FIG. 8 is a side view of a section of a knitted electrode assembly in accordance with embodiments of the present invention.

As noted above, an electrode assembly in accordance with embodiments of the present invention may be knitted into structures having a variety of shapes and dimensions. FIG. 8 illustrates a knitted electrode assembly 804 have an elongate tubular shape. In the embodiments of FIG. 8, electrode assembly 804 is knitted from a composite conductive filament 816 that is substantially similar to composite conductive filament 816 described above with reference to FIGS. 5A-5C. The conductive portion of composite conductive filament 816 forms electrode 806.

In the embodiments of FIG. 8, the knitted electrode assembly 804 has an inner diameter that is sufficient to receive an elongate support structure 852 therein. As shown, support structure 852 comprises a cylindrical member formed from a biocompatible, electrically non-conductive material that is sized to substantially fill the inner diameter of electrode assembly 804. Because support structure 852 substantially fills the inner diameter of electrode assembly 804, the knitted structure is disposed on the surface of the support structure, and support structure 852 provides additional mechanical strength to electrode assembly 804.

The inherent ability of the knitted electrode assembly to change diameter as it is compressed or expanded allows support structures 852 of various shapes and diameters to be easily introduced. This process may be further facilitated if composite conductive filament 816 has elastomeric properties.

As noted above, an electrode assembly in accordance with embodiments of the present invention comprises one or more electrodes to deliver electrical stimulation signals to, and/or receive signals from, a patient's tissue. Electrode assemblies in accordance with certain aspects of the present invention may also include one or more other active components configured to perform a variety of functions. As used herein, an active component refers to any component that utilizes, or operates with, electrical signals.

Figure 9:
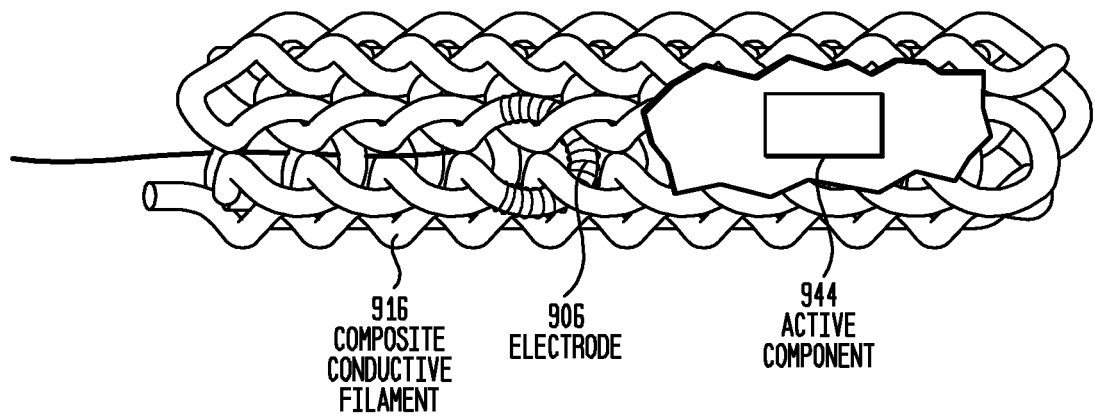
FIG. 9 is a side view of a section of a knitted electrode assembly in accordance with embodiments of the present invention.

FIG. 9 illustrates a knitted electrode assembly 904 in accordance with such embodiments of the present invention. In the embodiments of FIG. 9, electrode assembly 904 is knitted from a composite conductive filament 916 that is substantially similar to composite conductive filament 516 described above with reference to FIGS. 5A-5C. The conductive portion of composite conductive filament 916 forms electrode 906.

In FIG. 9, a section of the exterior surface of knitted electrode assembly 904 is cut away to expose an exemplary location for an active component 944 within the electrode assembly. For ease of illustration, active component 944 is schematically illustrated by a box. In accordance with embodiments of the present invention, active component 944 may comprise one or more instruments, apparatus, sensors, processors, controllers or other functional components that are used to, for example, diagnosis, monitor, and/or treat a disease or injury, or to modify the patient's anatomy or physiological process. Although FIG. 9 illustrates active component 944 as being disposed in electrode assembly 904, it should be appreciated that active component 944 may also be secured to the exterior surface of the electrode assembly, or positioned in other locations of the electrode assembly.

In one specific example, active component 944 comprises an agent delivery system for administering drugs, active substances or therapeutic agents (collectively and generally referred to as "therapeutic agents" herein) to a patient. In certain such embodiments, active component 944 may comprise a pump, reservoir and an agent delivery mechanism. In alternative embodiments, active component 944 comprises an agent delivery mechanism that is fluidically coupled to a pump and/or reservoir positioned outside electrode assembly 904. In one such embodiment, a cooling fluid is passed down the length of the electrode assembly for delivery to the electrode site for purposes of cooling the tissue which is adjacent to electrode 906. In another specific example, active component 944 includes one or more sensors for monitoring, for example, pressure, temperature, etc., within the patient.

In a still further embodiment of the present invention, the electrode assembly is knitted using a non-conductive filament that is an insulated conducting element which is suitable for strain gauge applications. In such embodiments, the electrode assembly may be constructed in one or more sections, each section being able to measure the strain experienced across that section. Other sensing devices may be incorporated into the structure using a similar method.

In another embodiment, active component 944 comprises one or more actuators incorporated into the knitted structure. Suitable actuators may include a low power linear motor. Such an actuator is anchored at a suitable location in electrode assembly 904 and may allow the electrode assembly to, for example, provide a method of applying pressure to an organ or body tissue for therapeutic benefit.

In a further embodiment, active component 944 comprises an enclosed electronics package. In this embodiment one of more electronics packages may be encapsulated in the knitted tube either during its manufacture or afterwards providing a compact and robust final assembly for the whole implantable device. In such embodiments, the one or more electronics packages function as the AIMD's electronics module.

Figure 10:
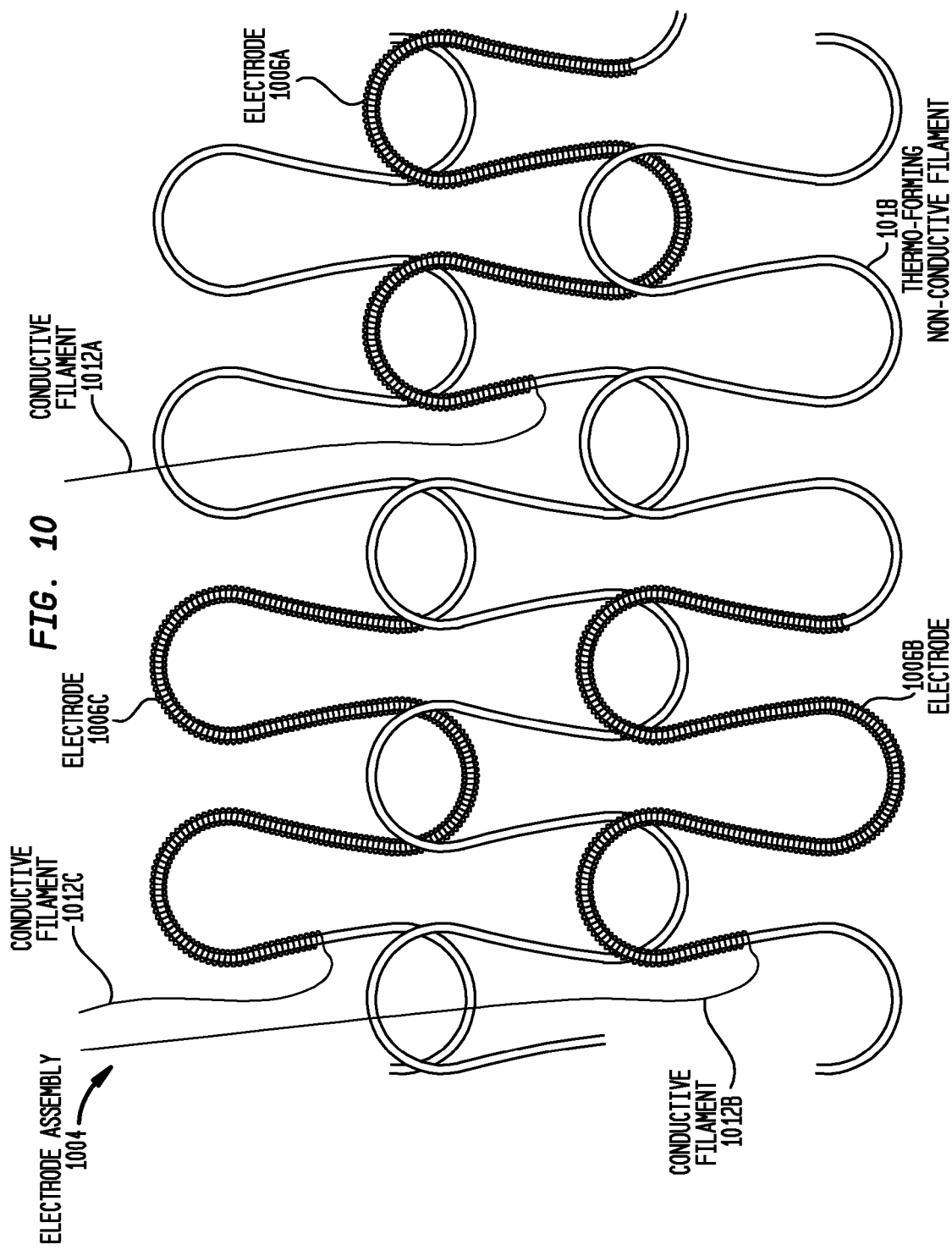
FIG. 10 is a perspective view of a section of a knitted electrode assembly molded into a desired shape in accordance with embodiments of the present invention.

As noted above, the above described knitting methods permit the formation of electrode assemblies having various shapes and sizes. In alternative embodiments of the present invention, a knitted electrode assembly is formed into a desired shape following the knitting process. FIG. 10 illustrates a section of an electrode assembly 1004 in accordance with such embodiments.

Electrode assembly 1004 is knitted in one of the manners described above from a thermo-softening plastic non-conductive filament 1018, and three conductive filaments 1012. Similar to the embodiments described above, following the knitting process electrode assembly 1004 has an elongate tubular shape. The illustrated section of electrode assembly 1004 includes three electrodes 1006 each formed by winding a section of conductive filaments 1012 around a section of non-conductive filament 1018, as described above with reference to FIGS. 5A-5C.

In the embodiments of FIG. 10, following the knitting process, electrode assembly 1004 is placed in a molding apparatus and heat is applied. Due to the use of a thermo-softening plastic non-conductive filament 1018, the applied heat causes the electrode assembly to take a desired shape. FIG. 10 illustrates embodiments in which a tubular electrode assembly has been flattened to form a substantially planar member. It should be appreciated that a variety of other shapes may also be formed using embodiments of the present invention.

Other methods for altering the shape of an electrode assembly are within the scope of the present invention. For instance, in one embodiment of the present invention, an electrode assembly may include one or more memory metal filaments, such as Nitinol, knitted into the assembly using one of the methods described above. In such embodiments, the memory metal filaments is be preformed to hold the electrode assembly in a first shape prior to implantation in a patient, but is configured to cause the electrode assembly to assume a second shape during or following implantation. The memory metal filaments may also be insulated as required.

In another embodiment of the present invention, one or more secondary suitable non-conductive filaments may be integrated along the length of the knitted structure. Such filaments are anchored securely at one point in the structure and incorporated loosely along the remaining length of the structure. These filaments may be used to manipulate the shape of the structure by applying appropriate tension to the various filaments as required.

In further embodiments, the shape of electrode assembly 1004 may be altered through sintering. For example, the structure may be laser sintered, and fiber crossing points within the structure may be formed into bending anisotropies. In other embodiments, electrode assembly 1004 may be processed (via molding, sintering, etc.) to create inflexible portions, such as a stiffened tip, or to create, for example, anchoring barbs that may be used to secure the electrode assembly to the patient.

FIG. 10 illustrates embodiments of the present invention in which the knitted structure is post-processed to form a different shape or configuration. It would be appreciated that in alternative embodiments the electrode assembly is dipped into, or molded over by, a second material to form a desired shape or configuration. For example, one or more portions of the electrode assembly may sealed with an added material to prevent the entry of body fluid into the structure. It would be appreciated that a number of different post-processing methods may be implemented to form the final structure.

In still further embodiments, following the knitting process an electrode assembly may be fully or partially covered by an outer structure, such as a tube. In such embodiments, the knitted structure would be stretched to reduce the width thereof, and the outer covering is placed over the desired portion. The knitted structure is then allowed to return to its previous non-stretched shape. The outer covering may be conductive, non-conductive or have both conductive and non-conductive sections, depending on the desired configuration. For example, an outer covering may be placed on the knitted structure such that conductive sections of the covering are disposed over the electrodes, while non-conductive sections extend over the other portions of the assembly. An outer structure may be beneficial to inhibit tissue growth into the knitted structure, to improve implantation by providing a smooth outer surface, to increase the surface area of conductive regions used to deliver electrical stimulation, increase stiffness of the assembly, etc.

Figure 11:
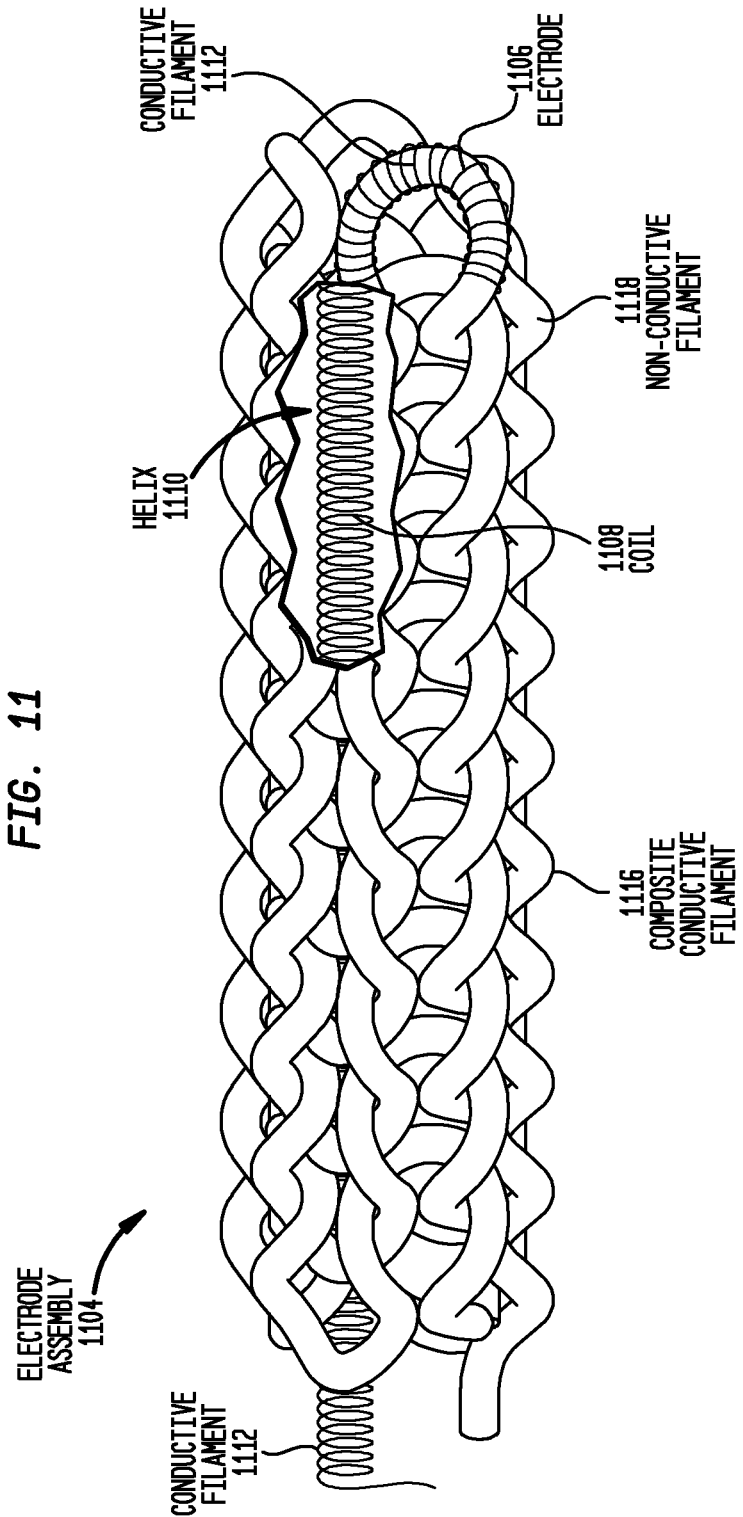
FIG. 11 is a side view of a section of a knitted electrode assembly in accordance with embodiments of the present invention.

As noted above, electrodes of an electrode assembly are electrically connected to an electronics module. However, implantable electrode assemblies are subject to bending and stretching during implantation, as well as during normal operation, that may damage or break the electrical connection between the electrodes and the electronics module. As such, embodiments of the present invention provide strain relief to protect the electrical connection. As used herein, a strain relief refers to a non-linear section of a wire or filament between the electrode and electronics module. Upon bending or stretching of the electrode assembly, the non-linear section of wire will expand to a longer length, thus preventing tension on the filament that results in a damaged electrical connection. FIGS. 11 and 12A-12B illustrate strain relief in electrode assemblies of the present invention.

FIG. 11 illustrates a knitted electrode assembly 1104 in accordance with embodiments of the present invention. Similar to the embodiments described above, electrode assembly 1104 has an elongate tubular shape. Furthermore, electrode assembly 1104 is formed from a composite conductive filament 1116 that is substantially similar to composite conductive filament 516 described with reference to FIGS. 5A-5C. Specifically, composite conductive filament 1116 is formed by winding a conductive filament 1112 around a section of a non-conductive filament 1118. The conductive portion of composite conductive filament 1116 (i.e. the section of conductive filament 1112 wound around non-conductive filament 1118) forms an electrode 1106.

In the embodiments of FIG. 11, conductive filament 1112 extends proximally from electrode 1106 through the interior of electrode assembly 1104 to an electronics module. In the embodiments of FIG. 11, this proximally extending portion of conductive filament 1112 is formed into a plurality of coils 1108, and is referred to as a helix 1110. Helix 1110 is a strain relief that prevents damage to the electrical connection between the electronics module and electrode 1106.

In specific embodiments of FIG. 11, electrode assembly 1104 is formed using a circular knitting method that is an inherently rotary process. Conductive filament 1112 is fed into the interior of electrode assembly 1104 as it being knitted, and the rotary motion is exploited to coil conductive filament 112 into helix 1110.

FIGS. 12A and 12B illustrate alternative methods in which the knitted structure is advantageously used to provide the strain relief. In the embodiments of FIG. 12A, electrode assembly 1204 has an elongate tubular shape. Electrode assembly 1204 is formed from a composite conductive filament 1216 that is substantially similar to composite conductive filament 516 described with reference to FIGS. 5A-5C. Specifically, composite conductive filament 1216 is formed by winding a conductive filament 1212 around a section of a non-conductive filament 1218. The conductive portion of composite conductive filament 1216 (i.e. the section of conductive filament 1212 wound around non-conductive filament 1218) forms an electrode 1206.

In the embodiments of FIG. 12A, conductive filaments 1212 are fed into the interior of electrode assembly 1204, but as the electrode assembly is knitted each conductive filament 1212 is woven through stitches in the assembly from the inside of the tube to the outside of the tube, and vice versa. As such, conductive filaments 1212 follow a serpentine path through electrode assembly 1204. This serpentine path provides non-linear sections of conductive filament that, when electrode assembly 1204 bends or stretches, will prevent damage to the electrical connection between electrodes 1206 and an electronics module.

In certain embodiments, conductive filaments 1212 are woven through successive stitches of successive courses such that the filaments follow a serpentine and helical path, as shown in FIG. 12A. The combination of the helical and serpentine path provides added strain relief.

FIG. 12B illustrates an alternative electrode assembly 1214 formed from first and second knitted tubes. A first knitted tube 1226 is formed from a biocompatible non-conductive filament 1238, and two conductive filaments 1222 are intertwined with the non-conductive filament. First knitted tube 1226 includes electrodes each formed by concurrently knitting a section of conductive filaments 1222 with sections of non-conductive filament 1238, as described above with reference to FIGS. 6A and 6B. For ease of illustration, the electrodes have been omitted from FIG. 12B.

Disposed in the center of first knitted tube 1226 is a second knitted tube 1228 knitted from a non-conductive filament 1248. Conductive filaments 1222 are woven in tube 1228 as described above with reference to FIG. 12A. In an alternative embodiment, conductive filaments 1222 may be knitted into a tube or plurality of tubes which form the inner tube or tubes in an exemplary multi-tube arrangement.

In the embodiments of FIG. 12B, the different tubes 1226, 1228, may be made of different materials to achieve different performance characteristics. For example, softer materials may be used in inner tubes to, for example, protect the electrical wires, while the outer tube may be constructed from a harder material for abrasion resistance or strength.

FIG. 13 is a side view of a section of a knitted electrode assembly 1304 in accordance with embodiments of the present invention. As shown, electrode assembly 1304 is knitted from a non-conductive filament 1338, and has two conductive filaments 1312 extending there through. Disposed on the surface of knitted electrode assembly 1304 are two electrodes 1306 formed by creating a ball or other shaped structure on the distal end of conductive filaments 1312. For example, in certain embodiments conductive filaments 1312 comprise platinum wire that is inserted into the knitted structure such that distal structure mates with the non-conductive filament, and is held in the appropriate position. The distal structure may be formed by, for example, melting the distal end of the conductive filament with a localized heat source, by bunching the conductive filament into the desired shape, attaching a bulk material piece (e.g. platinum foil) having the desired shape to the conductive filament by weld, crimping or other method, etc.

FIG. 14 is a perspective view of a composite conductive filament 1416 in accordance with embodiments of the present invention. In these embodiments, composite conductive filament is formed by cording two filaments around a non-conductive filament 1438. In these embodiments, two or more filaments 1412, at least one of which is conductive, are stitched around non-conductive filament 1412. FIG. 14 illustrates embodiments in two conductive filaments 1412 are stitched around non-conductive filament 1438. Both conductive filaments 1412 are used to redundantly connect an electrode formed there from to an electronics module. It would be appreciated that a variety of sewing methods may be used for cording, including zig-zag sewing with a lock stitch, sewing across the non-conductive filament with a chain stitch, overlocking two or more filaments, etc.

As noted above, aspects of the present invention are generally directed to an AIMD comprising an implantable, hermetically sealed electronics module and an electrode assembly formed using textile or fabric manufacturing methods.

Embodiments of the present invention have been primarily described herein with reference to form a single tubular structure. It would be appreciated that embodiments of the present invention may be used to form different or more complex structures, such as bifurcated or trifurcated tubes, depending on the desired therapeutic use.

In certain embodiments of the present invention, a biocompatible gel may be disposed within a knitted electrode assembly. The gel may substantially fill the electrode assembly, or at least fill a number of stitches of the electrode assembly. It should be appreciated that a variety of suitable gels, such as silicone, may be used in embodiments of the present invention. In certain embodiments, the gel may act as a barrier to tissue ingrowth. In other embodiments the gel may provide or reinforce desirable mechanical properties of the knitted structure, such as adding stiffness. The inclusion of gel within a knitted structure is shown in commonly owned and co-pending U.S. Utility Patent Application entitled "Knitted Catheter," filed Aug. 28, 2009, the contents of which are hereby incorporated by reference herein.

In further embodiments of the present invention, a tube may extend partially or fully through the knitted structure. The tube may be used to, for example, receive a removable stylet that assists in the implantation of the electrode assembly.

Also as noted above, different sizes and shapes of electrode assemblies may be manufactured in accordance with embodiments of the present invention. Each of these different sizes and shapes will require different amounts of filament to complete. However, the amount of filament generally required may be estimated for different arrangements. In particular, the amount of filament used in single stitch ($Y_s$) is given by the following Equation (1):

$$Y_s=(600/360) \cdot 2\pi \cdot r_s \qquad \text{Equation (1):}$$

Where $r_s$ is the radius of the stitch.

In embodiments in which a machine with a plurality of needles, of radius $r_n$, arranged in a circular fashion (radius=$r_m$) at an angular displacement of $\Theta$, the amount of filament of radius $r_y$ used in a stitch ($Y_s$) is given by Equation (2):

$$Y_s=2 \cdot r_m \cdot \sin(\Theta) \cdot C_n + r_n + \pi \cdot (r_n + r_y) \qquad \text{Equation (2):}$$

Where $C_n$ is a constant related to filament tension

Furthermore, in the embodiments of FIGS. 5A-5C in which a conductive filament is wound around a non-conductive filament as tightly as possible, the total length of conductive filament in one stitch ($C_s$) is given by Equation (3):

$$C_s=2\pi \cdot (r_{yc}+r_{nyc}) \cdot Y_s/(2r_{yc}) \qquad \text{Equation (3):}$$

Where: $r_{nyc}$=the radius of the non-conductive filament; $r_{yc}$=the radius of the conductive filamemy; and $Y_s$=the length of filament in one stitch from Equations (1) or (2). The surface area of the electrode created in this manner may be approximated by half the value $C_s$. The factor of one-half is used to account for the possibility that only the external part of the structure is available to interface with a patient's tissue.

The present application is related to commonly owned and co-pending U.S. Utility Patent Applications entitled "Knitted Electrode Assembly And Integrated Connector For An Active Implantable Medical Device," filed Aug. 28, 2009, "Knitted Catheter," filed Aug. 28, 2009, "Bonded Hermetic Feed Through For An Active Implantable Medical Device," filed Aug. 28, 2009, "Stitched Components of An Active Implantable Medical Device," filed Aug. 28, 2009, and "Electronics Package For An Active Implantable Medical Device," filed Aug. 28, 2009. The contents of these applications are hereby incorporated by reference herein.

While various embodiments of the present invention have been described above, it should be understood that they have been presented by way of example only, and not limitation. It will be apparent to persons skilled in the relevant art that various changes in form and detail may be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

What is claimed is:

1. An active implantable medical device (AIMD), comprising:
    an electronics module; and a knitted electrode assembly having an intermeshed loop structure, the knitted electrode assembly further comprising:
        at least one biocompatible, electrically non-conductive filament arranged in substantially parallel rows each row stitched to an adjacent row with one or more loops, and
        at least one biocompatible, electrically conductive filament intertwined with the at least one row of non-conductive filament, the at least one electrically conductive filament formed on an exterior surface of the electrode assembly to form an electrode on the exterior surface of the electrode assembly, and the at least one conductive filament configured to be electrically connected to the electronics module.

2. The AIMD of claim 1, wherein the at least one non-conductive filament consists of a single continuous non-conductive filament.

3. The AIMD of claim 1, wherein the at least one conductive filament consists of a plurality of conductive filaments each intertwined with separate rows of non-conductive filament.

4. The AIMD of claim 1, wherein a section of the at least one conductive filament is wound around a section of the one or more loops of the at least one non-conductive filament, and wherein the knitted electrode assembly consists of:
    substantially parallel rows of the at least one non-conductive filament having the conductive filament wound there around.

5. The AIMD of claim 1, wherein the at least one conductive filament is arranged in at least one row substantially parallel to a section of the at least one non-conductive filament.

6. The AIMD of claim 1, wherein the knitted electrode assembly is constructed and arranged as an elongate tube.

7. The AIMD of claim 6, wherein the knitted electrode assembly further comprises: a biocompatible, electrically non-conductive cylindrical support structure positioned in the knitted tube such that the tube is disposed on the surface of the support structure.

8. The AIMD of claim 1, wherein the electrode assembly forms a substantially planar sheet.

9. The AIMD of claim 1, further comprising: at least one active component positioned in the electrode assembly.

10. The AIMD of claim 9, wherein the at least one active component comprises an actuator.

11. The AIMD of claim 9, wherein the at least one active component comprises a hermetically sealed electronics package.

12. The AIMD of claim 1, wherein the at least one non-conductive filament comprises a drug-eluting polymer.

13. The AIMD of claim 1, wherein the at least one non-conductive filament comprises a thermo-softening plastic material.

14. The AIMD of claim 1, wherein the at least one non-conductive filament comprises an insulated conductive wire configured for use in measuring strain experienced by one or more sections of the electrode assembly.

15. The AIMD of claim 1, wherein a section of the conductive filament between the intertwined portion and the electronics module has a helical shape formed from coils.

16. The AIMD of claim 15, wherein the section of the conductive filament between the intertwined portion and the electronics module is woven into one or more loops of a plurality of the rows.

17. The AIMD of claim 1, wherein the electronics module is configured to generate electrical stimulation signals, and wherein the intertwined portion of the conductive filament is configured to deliver the stimulation signals to tissue of a recipient of the AIMD.

18. The AIMD of claim 1, wherein the intertwined portion of the conductive filament is configured to sense a nerve impulse generated by the tissue of the recipient, and to transmit an electrical signal representing the nerve impulse to the electronics module.

19. A method for manufacturing a knitted implantable electrode assembly having an intermeshed loop structure comprising:
providing at least one biocompatible, electrically non-conductive filament, and at least one biocompatible, electrically conductive filament; and
knitting the at least one non-conductive filament into substantially parallel rows each row stitched to and adjacent row with one or more loops, with the at least one conductive filament intertwined with the at least one row of non-conductive filament, the at least one electrically conductive filament formed on an exterior surface of the electrode assembly to form an electrode on the exterior surface of the electrode assembly, and the at least one conductive filament configured to be electrically connected to an electronics module.

20. The method of claim 19, wherein the at least one non-conductive filament consists of a continuous single non-conductive filament, and wherein the method comprises:
knitting the single non-conductive filament into substantially parallel rows each stitched to an adjacent row with the at least one conductive filament intertwined with the non-conductive filament.

21. The method of claim 19, wherein the at least one conductive filament consists of a plurality of conductive filaments, and wherein the method further comprises:
knitting the at least one non-conductive filament such that the plurality of conductive filaments are each intertwined with separate rows of the non-conductive filament.

22. The method of claim 19, further comprising:
winding the at least one conductive filament around a section of one or more loops of the at least one non-conductive filament prior to knitting; and
knitting the least non-conductive filament having the conductive filament wound there around into substantially parallel rows each stitched to an adjacent row.

23. The method of claim 19, further comprising:
concurrently knitting the at least one conductive filament with a section of the at least one non-conductive filament such that the at least one conductive filament forms at least one row substantially parallel to the section of at least one non-conductive filament.

24. The method of claim 19, wherein knitting the at least one non-conductive filament into the substantially parallel rows comprises:
circular knitting the at least one non-conductive filament into an elongate tube.

25. The method of claim 24, further comprising:
positioning a biocompatible, electrically non-conductive cylindrical support structure in the interior of the elongate tube.

26. The method of claim 19, wherein knitting the at least one non-conductive filament into the substantially parallel rows comprises:
flat knitting an electrode assembly to form a substantially planar sheet.

27. The method of claim 19, further comprising:
positioning one or more active components in the electrode assembly.

28. The method of claim 19, wherein providing the at least one non-conductive filament comprises:
providing at least one non-conductive filament comprising a drug-eluting polymer.

29. The method of claim 19, wherein providing the at least one non-conductive filament comprises:
providing at least one non-conductive filament that comprises a thermo-softening plastic material.

30. The method of claim 29, further comprising:
molding the electrode assembly into a desired shape.

31. The method of claim 19, wherein providing the at least one non-conductive filament comprises:
providing at least one insulated conductive wire configured for use in measuring strain experienced by one or more sections of the electrode assembly.

32. The method of claim 19, wherein the conductive filament is configured to be electrically connected to an electronics module, and wherein the method further comprises:
forming a section of the conductive filament between the intertwined portion and the electronics module into a helical shape using coils.

33. The method of claim 32, wherein the electrode assembly is a circular knit elongate tube, and wherein forming the section of the conductive filament into a helical shape comprises:
forming the helical shape during the circular knitting process.

34. The method of claim 32, further comprising:
weaving the section of the conductive filament between the intertwined portion and the electronics module into one or more loops of a plurality of the rows.

* * * * *

UNITED STATES PATENT AND TRADEMARK OFFICE
CERTIFICATE OF CORRECTION

PATENT NO.       : 8,923,984 B2  
APPLICATION NO.  : 12/549899  
DATED            : December 30, 2014  
INVENTOR(S)      : John L. Parker and David Robinson Page 1 of 1

It is certified that error appears in the above-identified patent and that said Letters Patent is hereby corrected as shown below:

In the Claims

Claim 19, Col. 17, line 27: "and" should read -- an --.

Signed and Sealed this  
Fourteenth Day of April, 2015

Michelle K. Lee  
*Director of the United States Patent and Trademark Office*